US009162084B2

(12) United States Patent
Vromen

(10) Patent No.: US 9,162,084 B2
(45) Date of Patent: Oct. 20, 2015

(54) FORMULATIONS FOR TOPICAL DELIVERY OF BIOACTIVE SUBSTANCES AND METHODS FOR THEIR USE

(75) Inventor: Jacob Vromen, Botany (AU)

(73) Assignee: CellMedics, Inc., Henderson, NV (US)

( * ) Notice: Subject to any disclaimer, the term of this patent is extended or adjusted under 35 U.S.C. 154(b) by 1853 days.

(21) Appl. No.: 11/535,213

(22) Filed: Sep. 26, 2006

(65) Prior Publication Data

US 2007/0071711 A1 Mar. 29, 2007

Related U.S. Application Data

(63) Continuation of application No. 10/281,062, filed on Oct. 25, 2002, now Pat. No. 7,241,456.

(51) Int. Cl.
*A61Q 17/04* (2006.01)
*A61Q 19/00* (2006.01)
*A61K 8/37* (2006.01)
*A61K 8/66* (2006.01)
*A61K 47/14* (2006.01)
*A61K 8/46* (2006.01)
*A61K 8/67* (2006.01)
*A61K 8/97* (2006.01)
*A61K 9/00* (2006.01)
*A61K 9/14* (2006.01)
*A61K 47/10* (2006.01)
*A61K 47/42* (2006.01)
*A61K 47/44* (2006.01)
*A61Q 17/00* (2006.01)

(52) U.S. Cl.
CPC . *A61Q 17/04* (2013.01); *A61K 8/37* (2013.01);
*A61K 8/46* (2013.01); *A61K 8/66* (2013.01);
*A61K 8/675* (2013.01); *A61K 8/676* (2013.01);
*A61K 8/97* (2013.01); *A61K 9/0014* (2013.01);
*A61K 9/145* (2013.01); *A61K 47/10* (2013.01);
*A61K 47/42* (2013.01); *A61K 47/44* (2013.01);
*A61Q 17/005* (2013.01); *A61Q 19/00*
(2013.01); *A61K 2800/28* (2013.01); *A61K 2800/31* (2013.01); *A61K 2800/412* (2013.01);
*A61K 2800/522* (2013.01); *A61K 2800/75* (2013.01)

(58) Field of Classification Search
CPC ........... A61K 8/37; A61K 8/66; A61K 8/676;
A61K 8/675; A61K 8/97; A61K 9/0014;
A61K 9/145; A61K 47/10; A61K 47/42;
A61K 47/44; A61K 8/46; A61K 2800/28;
A61K 2800/31; A61K 2800/412; A61K
2800/522; A61K 2800/75; A61Q 19/00;
A61Q 17/005; A61Q 17/04
USPC .............................................. 424/401, 74, 66
See application file for complete search history.

(56) References Cited

U.S. PATENT DOCUMENTS

| | | | |
|---|---|---|---|
| 4,011,319 A | 3/1977 | Kaiser et al. | 424/244 |
| 4,033,996 A | 7/1977 | Cragoe et al. | 260/490 |
| 4,127,118 A | 11/1978 | Latorre | 514/248 |
| 4,294,821 A * | 10/1981 | Neumiller | 424/45 |
| 4,440,777 A | 4/1984 | Zupan | 424/274 |
| 4,783,450 A | 11/1988 | Fawzi et al. | 514/78 |
| 4,801,587 A | 1/1989 | Voss et al. | 514/248 |
| 4,873,087 A | 10/1989 | Morishita et al. | 424/433 |
| 4,879,119 A | 11/1989 | Konno et al. | 424/449 |
| 4,963,367 A | 10/1990 | Ecanow | 424/485 |
| 5,153,179 A | 10/1992 | Eibl | 514/34 |
| 5,290,561 A | 3/1994 | Farhadieh | 424/449 |
| 5,352,456 A | 10/1994 | Fallon et al. | 424/448 |
| 5,372,819 A | 12/1994 | Godbey et al. | 424/449 |
| 5,399,355 A | 3/1995 | Riedl et al. | 424/448 |
| 5,409,706 A * | 4/1995 | Ramirez et al. | 424/401 |
| 5,411,734 A * | 5/1995 | Vargas et al. | 424/401 |
| 5,422,118 A | 6/1995 | Brown et al. | 424/449 |
| 5,460,821 A | 10/1995 | Masizq | 424/449 |
| 5,474,783 A | 12/1995 | Miranda et al. | 424/448 |
| 5,516,517 A | 5/1996 | Gardner | 424/401 |
| 5,607,691 A | 3/1997 | Hale et al. | 424/449 |
| 5,613,958 A | 3/1997 | Kochinke et al. | 604/307 |
| 5,660,839 A * | 8/1997 | Allec et al. | 424/401 |
| 5,837,289 A | 11/1998 | Grasela et al. | 424/484 |
| 5,869,030 A | 2/1999 | Dumler et al. | 424/59 |
| 5,962,018 A * | 10/1999 | Curtis et al. | 424/450 |
| 6,103,267 A | 8/2000 | Mitchnick et al. | 424/489 |
| 6,238,683 B1 * | 5/2001 | Burnett et al. | 424/405 |
| 6,416,769 B1 | 7/2002 | Vromen | 424/401 |
| 2001/0006645 A1 * | 7/2001 | Norton et al. | 424/400 |

(Continued)

FOREIGN PATENT DOCUMENTS

WO  WO 96 21422 A  7/1996
WO  WO 01 66092 A  9/2001

OTHER PUBLICATIONS

Coudray, Charles et al., Journal of Chromatographic Science, "Rapid High-Performance Liquid Chromatographic Assay for Salicylic Acid in Plasma Without Solvent Extraction", 34:166-173 (1996).
Carlin et al., Cosmetic Dermatology, pp. 35-58 (2001).
Greco et al., Plastic and Reconstructive Surgery, "Topical Vitamin C", 105:464-465 (2000).
Norman et al., Skin and Aging, "Do Alternative & Complementary Therapies Work for Common Dermatologic Conditions?", pp. 28-33 (2000).

(Continued)

*Primary Examiner* — Blessing M Fubara
(74) *Attorney, Agent, or Firm* — Verrill Dana LLP; Wayne A. Keown

(57) ABSTRACT

The invention relates to topical delivery of bioactive agents. More particularly, the invention relates to anhydrous formulations for percutaneous absorption. The invention provides formulations that allow efficient topical delivery of high concentrations of bioactive substances for percutaneous absorption. The formulations according to the invention are generally non-irritating to the skin.

2 Claims, No Drawings

(56) References Cited

U.S. PATENT DOCUMENTS

| | | | |
|---|---|---|---|
| 2001/0007653 A1 | 7/2001 | Moaddel et al. | 424/65 |
| 2001/0019722 A1* | 9/2001 | Fotinos et al. | 424/448 |
| 2002/0022052 A1 | 2/2002 | Dransfield | 424/449 |
| 2002/0028844 A1 | 3/2002 | Fitzpatrick et al. | 514/474 |
| 2002/0034489 A1* | 3/2002 | Wiegland et al. | 424/70.24 |
| 2002/0034536 A1* | 3/2002 | Perkins et al. | 424/450 |
| 2002/0086039 A1 | 7/2002 | Lee et al. | 424/401 |
| 2002/0160965 A1* | 10/2002 | Lanzendorfer et al. | 514/27 |
| 2002/0193321 A1* | 12/2002 | Vishnupad et al. | 514/29 |
| 2002/0197288 A1* | 12/2002 | Chevalier | 424/401 |
| 2003/0219391 A1* | 11/2003 | Liew et al. | 424/59 |

OTHER PUBLICATIONS

Martindale et al., The Extra Pharmacopia, 28$^{th}$ Ed., The Pharm. Press, London pp. 899-923 (1982).

Martindale et al., The Extra Pharmacopia, 29$^{th}$ Ed., The Pharm. Press, London pp. 6440661 (1982).

Chi et al., J. Pharm. Sci., "Release Rates of Ketoprofen from Poloxamer Gels in a Membraneless Diffusion Cell", 80(3):280-283 (1991).

Willimann et al., J. Pharm. Sci., "Lecithin Organogel as Matrix for Transdermal Transport of Drugs", 81(9):871-874 (1992).

Ballerini et al., J. Clin. Pharm. Res., "Study on the Absorption of Ketoprofen Topically Administered in Man: Comparison Between Tissue and Plasma Levels", VI(67-72 (1986) Abstract Only.

* cited by examiner

FORMULATIONS FOR TOPICAL DELIVERY OF BIOACTIVE SUBSTANCES AND METHODS FOR THEIR USE

RELATED APPLICATIONS

This application is a continuation of U.S. patent application Ser. No. 10/281,062, filed Oct. 25, 2002. The contents of which are incorporated herein by reference in its entirety.

BACKGROUND OF THE INVENTION

1. Field of the Invention

The invention relates to topical delivery of bioactive agents. More particularly, the invention relates to anhydrous formulations for percutaneous absorption.

2. Summary of the Related Art

Topical administration of biologically active agents has become an important method for treating a variety of skin conditions. Carlin, Cosmetic Dermatology, February 2001, pp. 35-38 teaches topical administration of vitamin C to reduce erythema of acne rosacea. Greco, Plastic and Reconstructive Surgery 105: 464-465 (2000) suggests the use of topical vitamin C in the treatment of fine wrinkles and as a stimulant for wound healing. Norman and Nelson, Skin and Aging, February 2000, pp. 28-33 teaches topical administration of a variety of common herbs to treat various dermatologic conditions. Unfortunately, many bioactive substances are not efficiently absorbed percutaneously. To overcome this problem, scientists have utilized low pH formulations or derivatives of bioactive substances. However, low pH formulations are irritating to the skin and derivatized compounds, while they may be more efficiently absorbed, are not generally efficiently bioconverted to yield the active compound. In addition, it is frequently difficult to obtain high concentrations of active in topical formulations, and in aqueous formulations, hydrophobic actives cannot be used.

There is, therefore, a need for new formulations that allow efficient topical delivery of high concentrations of underivitized bioactive substances for percutaneous absorbtion. Ideally, such formulations should be non-irritating to the skin.

BRIEF SUMMARY OF THE INVENTION

The invention provides formulations that allow efficient topical delivery of high concentrations of bioactive substances for percutaneous absorption. The formulations according to the invention are generally non-irritating to the skin.

In a first aspect, the invention provides formulations that are capable of efficient percutaneous absorption of high concentrations of hydrophobic, hydrophilic or ampiphilic bioactive substances. A great variety of bioactive substances may be included in the formulations according to the invention.

The formulations according to the invention comprise an anhydrous carrier medium, a high concentration of bioactive substance, and an exfoliant. Such formulations are free of any occlusive agent that prevents percutaneous absorption.

In a second aspect, the invention provides methods for using the formulations according to the invention to treat a dermatologic condition, the methods comprising applying therapeutically effective amounts of the formulations according to the invention to the skin.

In a third aspect, the invention provides a method for treating a dermatologic condition, the method comprising exfoliating the skin and applying to the skin a formulation comprising an anhydrous carrier medium and a high concentration of bioactive substance. The method may optionally include in the formulation an exfoliant. In a fourth aspect the invention provides a method for introducing a bioactive substance into the bloodstream of a patient. The method according to this aspect of the invention comprises applying therapeutically effective amounts of the formulations according to the invention to the skin.

In a fifth aspect the invention provides a method for introducing a bioactive substance into the bloodstream of a patient. The method according to this aspect of the invention comprises exfoliating the skin of a patient and applying to the skin a formulation comprising an anhydrous carrier medium and a high concentration of bioactive substance.

DETAILED DESCRIPTION OF THE PREFERRED EMBODIMENTS

The invention relates to topical delivery of bioactive agents. More particularly, the invention relates to anhydrous formulations for percutaneous absorption. The patents and publications cited herein reflect the knowledge in the art and are hereby incorporated by reference in their entirety. Any inconsistency between these patents and publications and this specification shall be resolved in favor of the latter.

The invention provides formulations that allow efficient topical delivery of high concentrations of bioactive substances for percutaneous absorption. The formulations according to the invention are generally non-irritating to the skin, in spite of high concentration, which may cause slight tingling of a passive nature due to the heightened activity.

The formulations according to the invention provide many advantages over aqueous formulations. For example, acidic or basic biological actives in an aqueous environment will at high concentrations affect the pH of the formulation, thus rendering it irritating to the skin. In an anhydrous environment, ionization does not occur, so high concentrations of such actives may be achieved in a formulation that does not irritate the skin. This is advantageous because one of the governing factors for percutaneous absorption is the concentration of the biological active, with higher concentrations leading to increased percutaneous absorption.

Some embodiments of the formulations according to the invention provide the further advantage of providing the biological active in a particle size that approximates the molecular size of the biological active. This is advantageous because the size of the biological active is another governing factor for percutaneous absorption. As particle size decreases, percutaneous absorption increases.

Another advantage provided by the anhydrous formulations according to the invention is increased stability of the biological active. Hydrophilic biological actives are frequently labile when exposed to water. They are prone to oxidation, hydrolysation and decomposition. In the formulations according to the invention, they are not. Also, in some embodiments of the invention, this stability is further enhanced by coating the molecular-sized particles with protective oils. This allows non-derivatized (i.e., not covalently modified) biological actives to be used and prevents coalescence of particles. Since bioconversion of covalently derivatized biological actives is generally inefficient, this provides greater activity for the biological active.

Yet another advantage provided by the anhydrous formulations according to the invention is that they efficiently partition hydrophilic biological actives for percutaneous absorption, because the hydrophilic molecules prefer the hydrophilic environment of the dermis to the hydrophobic environment of the anhydrous formulation.

An additional advantage provided by the formulations according to the invention is that they exfoliate the skin as they are applied. By removing dead skin cells of the stratum corneum without damaging underlying keratinocytes and fibroblasts, percutaneous absorption is further enhanced. In some embodiments of the invention, this effect is increased through the use of penetration enhancers that reversibly alter the physiochemical nature of the stratum corneum to reduce its diffusional resistance.

In a first aspect, the invention provides formulations that are capable of efficient percutaneous absorption of high concentrations of hydrophobic, hydrophilic or amphoteric bioactive substances. A great variety of bioactive substances may be included in the formulations according to the invention. For purposes of the invention, "percutaneous absorption" means penetration of the stratum corneum by the bioactive substance in active form. "Active form" means that the bioactive substance is capable of performing its physiological role.

The formulations according to the invention comprise an anhydrous carrier medium, a high concentration of micronized bioactive substance, and an exfolient. In certain embodiments, such formulations further comprise a penetration enhancer. Such formulations are preferably free of any occlusive agent that prevents percutaneous absorption, such as silicones. In preferred embodiments the micronization may be wet micronization or dry micronization. For purposes of the invention, an "anhydrous carrier medium" is a substance that is substantially free of water. "Substantially free of water" means that water that is present, if any, is in insufficient amount to affect either percutaneous absorption or the activity or stability of the bioactive substance. Preferred anhydrous carriers include, without limitation, esters, amides, ethoxylated fats, mineral oil, petrolatum, vegetable oils, animal fats, triglycerides, polyols (e.g., glycerol), glycerin, propylene glycol and sorbitol. Glycerin in concentrations of 20-40%, 25-35% and about 35% are among the preferred embodiments. In certain preferred embodiments the exfolient is non-irritating. In certain preferred embodiments the bioactive substance is non-derivitized.

A "high concentration" is a concentration that is therapeutically effective, as defined for the second aspect of the invention. In many cases, such concentration exceeds the concentration of the bioactive substance obtainable in an aqueous medium under conditions that are not irritating to the skin. "Non-derivativitized" means that the bioactive substance is in its native form and has not been covalently modified, e.g., through esterification, etc.

In certain embodiments, the formulations may be manufactured by standard "dry" micronization procecess. According to certain preferred methods of manufacturing the preferred formulations, the bioactive substance, preferably in powder form is subjected to a "wet" micronization process, as made available by Microniser Pty. Ltd. of Dandenong, Australia/Micronisers of Australia of Melbourne, Australia. Wet micronization prevents overheating of the active, the coating prevents coalescence of particles and protects against oxidation, reduction and hydrolysis. This process, which may be contrasted to so-called "dry" or standard micronization processes, preferably involves the grinding of the powder, suspended in or otherwise in the presence of a non-aqueous liquid, preferably an oil (hereinafter, the "suspending medium"). The process is preferably conducted in an abrasion-resistant container in the presence of a grinding medium, using sufficiently high rpm for a sufficiently long duration, and a suitable stirrer. The resulting suspension may be separated from the grinding medium by suction filtration of the powder. This micronization process is capable of producing particles of bioactive substance having a mean particle size corresponding to the molecule size of the bioactive substance.

Alternatively, the grinding may be conducted in the presence of 0.1 to 30%, and preferably 0.5 to 15% by weight, of a grinding aid such as an alkylated vinylpyrrolidone polymer, a vinylpyrrolidone-vinylacetate copolymer, an acylglutamate, an acrylate-tert.-octylpropenamide copolymer, a ditolylether sulphonic acid-formaldehyde condensate, a carbomer, a commercial mixture of fatty acid esters comprising a nonionic precursor such as tristyrylphenol ethoxylate or, in particular, a phospholipid, as described in U.S. Pat. No. 5,869,030.

The suspending medium is most preferably a vegetable oil, which promotes (along with the physical micronization process, as described above) breaking the bioactive substance into ultrafine particles and, at the same time, coating the particles with the oil, which promotes maximum absorbance and stability of the bioactive substance in the formulation. The micronized bioactive substance particles used preferably exhibit a mean particle size of no more than approximately 5 μm, and preferably a mean particle size of in the range of from about 0.01 to about 2 μm, and most preferably from about 0.05 to about 1.5 μm, and especially from about 0.1 to about 1.0. μm.

Oils most preferable and therefore most suitable for use include, without limitation, caprylic triglycerides, capric triglycerides, isostearic triglycerides, adipic triglycerides, propylene glycol myristyl acetate, lanolin oil, polybutene, isopropyl palmitate, isopropyl myristate, diethyl sebacate, diisopropyl adipate, hexadecyl stearate, cetyl oleate, oleyl alcohol, hexadecyl alcohol, wheatgerm oil, vegetable oils such as castor oil, corn oil, cottonseed oil, olive oil, palm oil, coconut oil, palm kernel oil, canola oil, sunflower oil, safflower oil, meadow foam oil, jojoba oil, hydrogenated vegetable oils, and mineral oil. In one preferred embodiment, the bioactive substance is micronized in the presence of capric/caprylic glycerides in which the bioactive substance is present at high concentrations.

A "bioactive substance" (sometimes referred to as a "biological active") is a substance that exerts some physical effect upon the skin. Such bioactive substances may provide protective functions, such as protection from exposure from radiation (e.g., from sunlight) or chemical exposure. The bioactive substance may serve a therapeutic role for the treatment of a dermatological condition, or may provide a micronutrient. Many bioactive substances are discussed herein. However, those skilled in the art will recognize that other well known bioactive substance, or any bioactive substance developed in the future can readily be incorporated into the topical delivery formulations according to the invention. The skilled artisan will also recognize that combinations of different bioactive substances can readily be incorporated into the topical delivery formulations according to the invention.

In certain embodiments the bioactive substance is a vitamin or a micronutrient. Preferred vitamins or micronutrients include, without limitation, vitamin C, vitamin E, vitamin B12, vitamin B6, folic acid, beta carotene and niacin or combinations thereof. A combination of vitamin C and vitamin E is one preferred embodiment. This preferred embodiment may further include niacin. Niacin in combination with an anti-inflammatory agent is another preferred embodiment. Preferred anti-inflammatory agents include, without limitation, aspirin, ibuprofen and acetaminophen and cox-2 inhibitors.

In certain embodiments the bioactive substance is an antimicrobial or antiviral antibiotic. Preferred antimicrobial antibiotics include antibacterial antibiotics antiparasitic antibiotics and antifungal antibiotics. Preferred fungicides include, without limitation, butocouazole nitrate, haloprogen, clotrimazole and other azoles. Preferred antivirals include, without limitation, O-[(2-hydroxyetoxy)-methyl]guanine and other herpes treatment medications, and tee tree oil (oil of *Melaleuca* spp.).

In certain embodiments the bioactive substance is an antioxidant selected from, without limitation, urocanic acid and other imidazoles; D,L-carnosine, D-carnosine, L-carnosine, anscrine and other peptides; alpha-carotine, beta-carotine, lycopine and other carotines; carotenoids; dihydrolipoic acid and other lipoic acids; aurothioglucose, propylthiouracil, thioredoxin, glutathion, cysteine, cystine, cystamine and other thiols; dilauryl thioproponate; distearyl thiopropionate; thiopropionate; thiopropionic acid; butathione-sulfoxamines, homocysteine-sulphoxamine, butathione-sulphones, penta-, hexa- and heptathioninesulphomimine and other sulfoxamine compounds; alpha-hydroxy-fatty acids, palmitic acid, lactoferrin, EDTA, EGTA and other metal chelating agents; citric acid, lactic acid, malic acid and other alpha-hydroxy acids; gamma-linolenic acid, linoleic acid, oleic acid and other unsaturated fatty acids; folic acid; ubiquinone, ubiqinol and other quinones; vitamin C; ascorbyl palmitate, Mg ascorbyl phosphate, ascorbyl acetate and other vitamin C derivatives; vitamin E acetate and other tocopherols and tocopherol derivatives; retinoids; vitamin A; vitamin A palmitate and other vitamin A derivatives; coniferyl benzooate of benzoin resin; rutic acid; alpha-glycosylrutin; ferulic acid furfurylideneglucitol; carnosine; butylhydroxytoluene (BHT); butylhydroxyanisole (BHA); nordihydroguaic resin acid; nordihydroguaiaretic acid; trihydroxybuterophenone; uric acid; mannose; ZnO, $ZnO_4$ and other zinc compounds; selenium and stilbenes.

In certain embodiments the bioactive substance is a sugar, an amino acid or a small peptide, including, without limitation carnosine, acetyl-L-carnitine, N-acetyl-carnitine, N-acetyl-cysteine, N-acetyl-D-glucosamine, B/D/L-alanine, alpha-keto-glutarates, arginates, L-arganine base/HCl, L-arginine-pyroglutamate, ascorbates, L-aspargine monohydrate, aspartame, aspartates, L-aspartic acid, L-carnitine base, L-carnitine fumarate, L-carnitine/HCl, L carnitine bitartrate, L-carnitine-L-tartrate, chelates, L-citruline, creatin monohydrate, creatin phosphate, creatine pyruvate, L-cysteine base, L-cysteine/HCl monohydrate, anhydrous L-cysteine/HCl, cysteinates, N,N-dimethylglycine base/HCl, glutamates, L-glutamic acid, L-glutamine, L-glutamine peptide, reduced L-glutathione, L-glycine, keto-glutaric acid, L-histidine base/HCl, L-isoleucine, L-leucine, lysinates, L-lysine monohydrate/HCl, D-mannose, DL/L-methionine, L-ornithine/HCl, DL/L-phenylalanine, L-hydroxyproline, trans-hydroxy-L-proline, pyroglutamic acid, D/L-ribose, L-selenium-methionine, L-serine, taurates, tartarates, L-threonine, trimethylglycine, DL/L-tryptophan, taurine, L-theanine, L-tyrosine, L-valine, xylitol, D-xylose, DL/L-zinc monomethionine, and all other D or L-amino acids and short peptides and all bases, acids and salts thereof. In certain embodiments the antioxidant may be an antioxidant derivative. Preferred derivatives include, without limitation, esters, ethers, peptides, lipids, nucleotides and nucleosides of such antioxidants. Preferred derivatives also include glycosyl, N-acetyl, methyl, ethyl, propyl, amyl, butyl lauryl, palmitoyl, oleyl, gamma-linoloyl, cholesteryl and glyceryl esters of such antioxidants.

In certain embodiments the bioactive substance is a biological additive. As used herein, the term "biological additive" indicates any compound obtained from a natural source, including plants, animals, bacteria and yeast, which has a medicinal or otherwise beneficial effect when topically applied to the skin. Examples of biological additives include, without limitation, oil of *Melaleuca* spp. (tea tree oil), oil of *Lavandula angustifolia, Carica papaya* extract, *Echinacea angustifolia* extract, *Mimosa tenuiflora* extract, *Hydrocotyl (centella) asiatica* extract, *gingko biloba* extract, *Matricaria chamomila* (chamomile oil) extract, *Hypericum perforatum* extract, *Aloe barbedensis* extract, and the like. The biological sources for "biological additive" may also include, but are not limited to the following: Aloe Vera, (e.g., *Aloe Barbedensis*); Arnica, (e.g., *Arnica Montana*); Bladderwrack (seaweed), (e.g., *Fucus Vesciculosis*); Birch, (e.g., *Betula Alba*) (*Pendula*); Chamomile, (e.g., *Matricaria Chamomila, Chamomila Recutita*); Marsh Mallow, (e.g., *Althea Officinalis*); Meadow Sweet, (e.g., *Spirea Ulmaria*) (*Filipendula*); Mint/Lemon Balm, (e.g., *Melissa Officinalis*); Mimosa, (e.g., *Mimosa Tenuiflora*); Myrrh Tincture, (e.g., *Commiphor Myrrha*); Neem, (e.g., *Melia Azadirachta*); Nettle (stinging), (e.g., *Urtica Dioica*); Papaya, (e.g., *Carica Papaya*); Propolis (bee glue), (e.g., *Propolis Cera*); Raspberry, (e.g., *Rubis Idaeus*); Red Poppy, (e.g., *Papaver Rhoeas*); Rose Hip (dog rose), (e.g., *Rosa Carima*); Rosemary, (e.g., *Rosemarinus Officinalis*); Sage, (e.g., *Salvia Officinalis*); St. Johns Wort, (e.g., *Hypericum Perforatum*); Strawberry, (e.g., *Fragaria Vesca*); Thea Sinensis (green tea), (e.g., *Camelia Sinensis*); Walnut, (e.g., *Juglans Regia*); Witchhazel (dist/extr), (e.g., *Hamamelis Virginiana*); Yarrow, (e.g., *Achillea Millefolium*); Wild Yam, (e.g., *Dioscorea Villosa*); Hawthorn, (e.g., *Crataegus Monogina/Oxyantha*); Herma (black/rod), (e.g., *Lawsoma Ehemus*); Hops, (e.g., *Humulus Lupulus*); Horse Chestnut, (e.g., *Aesculus Hippocastanum*); Horse Tail, (e.g., *Equisitum Arvense*); Ivy, (e.g., *Hedera Helix*); Linden/Lime Tree Blossoms, (e.g., *Tilia Argentea Cordata*); Madder, (e.g., *Rubia Tinctorum*); Marigold, (e.g., *Calendula Officinalis, Centella Asiatica, Centella Asiatica Urban, Hydrocotyl Asiatica*); Carrot (roots), (e.g., *Daucus Carota*); Comfrey (*Allantoine*), (e.g., *Symphytum Officinale*); Coneflower (*Echinacea*), propolis (e.g., *Echinacea Angustifolia*); Cucumber, (e.g., *Cucumis Sativus, Frucus Cucumis*); Fenugreek, (e.g., *Trigonella Foenum Greacum*); Gingko, (e.g., *Gingko Biloba*); Ginseng, (e.g., *Panax Ginseng*); Great Burdock, (e.g., *Radix Bardanea/Arctium Lappa*); Tea Tree Oil, (e.g., Oil of *Melaleuca Alternifolia*); Colts Foot, (e.g., *Tussilago Farfara*); Clover, arbutui (e.g., *Trifolium Pratense*); Speedwell, (e.g., *Veronica Officinalis*). A particularly preferred biological additive is tea tree oil. In a preferred embodiment, one or more biological additive is present in the formulation in a combined amount of from about 1% to 10% by weight, more preferably from about 2% to 8% by weight, and most preferably from about 4% to 6% by weight.

In certain embodiments the bioactive substance is a sunblock. In certain embodiments the sunblock is not a UV absorber. Preferred sunblocks include, without limitation, dioxybenzone, ethyl 4-[bis(hydroxypropyl)]aminobenzoate, glyceryl aminobenzoate, homosalate, menthyl anthranilate, octocrylene, octyl methoxycinnamate, octyl salicylate, oxybenzone, padimate O, red petrolatum, titanium dioxide, 4-methylbezylidene camphor, benzophenone-1, benzophenone-2, benzophenone-6, benzophenone-12, isopropyl dibenzoyl methane, butylmethoxydibenzoylmethane, zotocrylene, zinc oxide, para-aminobenzoic acid, cinnamate; and derivatives, analogs and functional analogs of such sunblocks.

In certain embodiments the bioactive substance is a local anesthetic. Preferred local anesthetics include, without limitation, lidocaine and procaine. See also Martindale, *The Extra*

*Pharmacopia*, Twenty-eighth Edition, The Pharmaceutical Press, London (1982), pp. 899-923.

For purposes of the invention, an "exfoliant" is a substance that eliminates dead cells from the stratum corneum without killing underlying living skin cells. In certain embodiments the exfoliants are chemical exfoliants, such as AHA and BHA. In certain preferred embodiments, the exfoliating agents are enzymes. One preferred enzyme is papain, an enzyme obtained from unripe papaya. One particularly preferred form of papain is Linked-Papain™ (papain carbomer, as described in CTFA, the International Cosmetic Ingredients Dictionary) in which papain is covalently immobilized to 1% polyacrylic acid (900,000 daltons), commercially available from Collaborative Laboratories, 3 Technology Drive, East Setauket, N.Y. 11733). In a preferred embodiment, the enzyme is present in the formulation in an amount between about 1% and 7%, more preferably between about 2% and 6%, most preferably about 5% by weight. The ability of papain to act as an exfoliant allows enhancement of percutaneous absorption of any desired bioactive substance. Other preferred enzymes include, without limitation, serine proteases, macramidase, penicillinase, pepsin, plasmin, bromelains, streptokinase, sutilains, trypsin, urokinase, keratinase, amylase, hyaluronidase, cholic acid, chymopapain, chymotrypsin, cynara, brinolase and chenodeoxycholic acid. See also Martindale, *The Extra Pharmacopia*, Twenty-eighth Edition, The Pharmaceutical Press, London (1982), pp. 644-661.

Certain preferred embodiments of the topical delivery formulations according to the invention include penetration enhancers. For purposes of the invention, a "penetration enhancer" is an agent that increases skin permeability by revaersibly altering the physiochemical nature of the the stratum corneum to reduce its diffusional resistance. Preferred penetration enhancers include, without limitation, oxazolidinones, propylene glycol, epidermal enzymes, oleic acid, dimethyl isosorbide, dimethylsulfoxide, ethanol, diethylene glycol monoethyl ether, hyaluronic acid, chitin, mucopolysaccharides, unsaturated fatty acids, linoleic acid, alpha linoleic acid, cod liver oil, menthol derivatives, squalene, glycerol derivatives, glycerol monoethers; chamomile flavones apigenin, lutrolin, apigenin 7-O-beta-glucoside and other herbal ingredients. Without wishing to be bound by theory, the inventor believes that such penetration enhancers act through one or more of the following mechanisms: increasing the fluidity of the stratum corneum lipids and reducing the diffusional resistance to permeants; removing intercellular lipids and dialation between adherent cornified cells; increasing the thermodynamic activity of drugs in vehicles; exfoliating stratum corneum cell membranes; dissociating adherent cornified cells and elimination of the barrier function.

In a second aspect, the invention provides methods for using the formulations according to the invention to treat a dermatologic condition, the methods comprising applying the formulations according to the invention to the skin. The formulations are applied at a therapeutically effective concentration. A "therapeutically effective concentration" is a concentration that eliminates or reduces recognizable clinical manifestations of a dermatological condition. A "dermatological condition" is an abnormality of the skin. Dermatological conditions include, without limitation, acne, bruises, burns, eczema, mycoses, pruritis, psoriasis, seborrhea, scabs, shingles, tineapedis, wounds, wrinkles and erythema of acne rosacea. Preferred agents for treating dermatological conditions include, without limitation, anti-acne preparations; anti-inflammatory agents; monobenzone and other depigmenting agents; amcinonide, diflorasone diacetate, hydrocortisone and other dermatitis relief agents; methylbenzethonium chloride and other diaper rash relief agents; mineral oil, PEG-4 dilaurate, lanolin oil, petrolatum, mineral wax and other emolients and moisturizers; alclometasone dipropionate, betamethasone valerate, isopropyl myristate MSD and other pruritic medications; anthralin, methoxsalen, coal tar and otherpsoriasis, seborrhea and scabicide agents; 2-(acetyloxy)-9-fluoro-1',2'3'4'-tetrahydro-11-hydroxypregna-1,4-dieno[16,17b]napthalene-3,20-dione, 21-chloro-9-fluoro-1',2',3',4'-terahydro-11b-hydroxypregna-1,4-dieno[16z,17b]napthalene-3,20-dione and other steroids.

In certain embodiments, the method according to this aspect of the invention, the method further includes preventing the formulation according to the invention from escaping to the exterior of the skin. Preferred methods for achieving this include covering the area of the skin that has been treated with a formulation according to the invention with an occlusive patch or other occlusive agent.

In a third aspect, the invention provides a method for treating a dermatologic condition, the method comprising exfoliating the skin and applying to the skin a formulation comprising an anhydrous carrier medium and a high concentration of a bioactive substance. The method may optionally include in the formulation an exfoliant, preferably a non-irritating exfoliant. Exfoliation of the skin may be chemical, mechanical or enzymatic. Chemical and enzymatic exfoliation have been discussed previously. Mechanical exfoliation may be carried out by any mechanical frictional force, including, without limitation, brushing, washing or particle pressure. In certain preferred embodiments, the formulation contains a wet-micronized bioactive substance. The term "dermatologic condition" is as described previously.

In certain embodiments, the method according to this aspect of the invention, the method further includes preventing the formulation according to the invention from escaping to the exterior of the skin. Preferred methods for achieving this include covering the area of the skin that has been treated with a formulation according to the invention with an occlusive patch or other occlusive agent.

In a fourth aspect the invention provides a method for introducing a bioactive substance into the bloodstream of a patient. The method according to this aspect of the invention comprises applying therapeutically effective amounts of the formulations according to the invention to the skin.

In certain embodiments, the method according to this aspect of the invention, the method further includes preventing the formulation according to the invention from escaping to the exterior of the skin. Preferred methods for achieving this include covering the area of the skin that has been treated with a formulation according to the invention with an occlusive patch or other occlusive agent.

In a fifth aspect the invention provides a method for introducing a bioactive substance into the bloodstream of a patient. The method according to this aspect of the invention comprises exfoliating the skin of a patient and applying to the skin a formulation comprising an anhydrous carrier medium and a high concentration of bioactive substance.

In certain embodiments, the method according to this aspect of the invention, the method further includes preventing the formulation according to the invention from escaping to the exterior of the skin. Preferred methods for achieving this include covering the area of the skin that has been treated with a formulation according to the invention with an occlusive patch or other occlusive agent.

The following examples are intended to further illustrate certain particularly preferred embodiments of the invention and are not intended to limit the scope of the invention in any way.

EXAMPLE 1

Preparation of a Formulation for Percutaneous Absorption

TABLE 1

Preferred concentrations

|  | Examples of agents | Purpose | Conc. |
|---|---|---|---|
| Anhydrous Medium | Glycerin | Humectant | 35% |
|  | propylene glycol | skin conditioner | 10% |
|  | capric-caprylic triglyceride | emollient | 10% |
|  | cetearyl alcohol | viscosity increasing agent | 4.5% |
|  | ceteth-20 | surfactant | — |
|  | d-tocopherol | antioxidant | 0.6% |
|  | apricot kernel oil | skin conditioner | — |
|  | sweet almond oil | skin conditioner | — |
|  | ascorbyl palmitate | antioxidant | 0.6% |
|  | thiodiproprionic acid | antioxidant | 0.6% |
|  | BHT | antioxidant | 0.3% |
|  | Phenoxyethanol | preservative | 0.6% |
|  | Methyl/ethyl/propyl/butyl parabens | preservatives | 0.3% |
|  | Strawberry extract | fragrance | — |
| Bioactive substance | Ex. 1: micronized niacin-nicotinic acid (nicotinamide) in capric/caprylic triglyceride |  | 4% |
|  | 50% acetylsalicylic acid micronized in capric/caprylic triglyceride |  | 5% |
|  | micronized L-ascorbic acid in capric/caprylic triglyceride |  | 25–30% |
|  | Ex. 2: 50% acetylsalicylic acid micronized in capric/caprylic triglyceride |  | 10% |
|  | Ex. 3: L-carnosine micronized in capric/caprylic triglyceride |  | 4–5% |
|  | Micronized L-ascorbic acid in capric/caprylic triglyceride |  | 25–30% |
|  | Ex. 4: Extracts in propylene or butylenes glycol: |  |  |
|  | Witch hazel |  | 8% |
|  | Horse chestnut |  | 0.5% |
|  | Arnica |  | 0.5% |
|  | Chamomile |  | 0.5% |
|  | Corn poppy |  | 0.5% |
|  | Ex. 5: Lidocaine micronized in capric/caprylic triglycerides |  | 5% |
| Exfoliant | papain carbomer |  | 5% |

EXAMPLE 2

Application of a Formulation for Percutaneous Absorption

Patients were 40-55 years of age with significant wrinkling and photo-damage. Composition for topical administration contained 30% wet micronized (in capric/caprylic triglyceride) L-ascorbic acid, 2% alpha-tocopheral, 35% glycerin and 5% papain carbomer. This composition was applied sparingly to the affected area and gently massaged into the skin every other night. The area was moisturized on alternate (non-treatment) nights. Treatment was repeated over a 90 day course. Substantial improvement of wrinkling and photo-damage was observed.

EXAMPLE 3

Application of a Formulation to Obtain Blood Levels of Active

Balb/c mice are obtained and shaved in the dorsal area. The composition is 50% acetylsalicylic acid wet micronized in capric/caprylic triglyceride; 35% glycerin and 5% papain carbomer. The composition is applied sparingly into the shaved area and gently massaged into the skin. One hour later, plasma is obtained and acetylsalicylic acid is measured by the method of Coudray et al., J. Chromatogr. 34: 166-173 (1996). Briefly, aliquots (400 µL) of serum are acidified with 75 µL concentrated HCl (35%) in 10×70 mm glass tubes. The samples are vortexed for 30 seconds, then 3 mL ether is added and the solution is extracted for 2 minutes. The tubes are centrifuged at 1600×g for 15 minutes, then 2 mL of ether phase is removed and dried under a nitrogen steam. The dry residue is reconstituted in 200 µL of mobile phase (85% methanol, sodium citrate and acetate at pH5.45) and loaded into a reversed phase HPLC column (5 µm ultrasphere octadecyl silane; Alltech, Paris, France). Flow rate is 1 mL/minute and detection is at 295 nm. It is expected that acetylsalicylic acid will be detected in the sample.

What is claimed is:

1. An anhydrous topical cream delivery formulation for percutaneous absorption consisting essentially of capric/caprylic triglyceride, glycerol, beta hydroxy acid, and one or more diethylene glycol monoethyl ether, dimethyl isosorbide, propylene glycol, oleic acid, epidermal enzymes, ethanol and dimethylsulfoxide.

2. The anhydrous formulation according to claim 1, wherein the glycerol is present in a concentration of 20%-40%.

* * * * *